United States Patent [19]
Mekhtiev et al.

[11] 4,062,885
[45] Dec. 13, 1977

[54] PROCESS FOR PRODUCING PHTHALONITRILE

[76] Inventors: Soltan Dzhafarovich Mekhtiev, ulitsa Khagani, 26/32, blok 5, kv. 92; Ramiz Gasan Kuli Ogly Rizaev, ulitsa Sharif-zade, 148, blok 5, kv. 67; Adilya Shir Mamed Kyzy Novruzova, ulitsa Shaumiana, 59, blok 3, kv. 42; Roida Jusuf Kyzy Magerramova, ulitsa 12 Nagornaya, 123, blok 1, kv. 9; Geibat Nagmetovich Suleimanov, ulitsa 4 Khrebtovaya, 558 kvartal, blok 1, kv. 7; Murshud Sary Ogly Rafiev, poselok 8 kilometr, ulitsa Nasimi, 33, blok 3, kv. 33; Fikret Dzhabrail Ogly Guseinov, ulitsa A. Aslanova, 115, kv. 73; Viktor Efimovich Sheinin, ulitsa Pervomaiskaya, 251, blok 2, kv. 28, all of Baku, U.S.S.R.

[21] Appl. No.: 697,253

[22] Filed: June 17, 1976

[51] Int. Cl.$^2$ .................................... C07C 120/14
[52] U.S. Cl. ........................... 260/465 C; 252/467
[58] Field of Search ............................ 260/465 C

[56] References Cited

U.S. PATENT DOCUMENTS

| 3,393,220 | 7/1968 | Winnick et al. | 260/465 |
| 3,870,743 | 3/1975 | Ibing et al. | 260/465 C |

Primary Examiner—Dolph H. Torrence

[57] ABSTRACT

A process for producing phthalonitrile, which comprises reacting o-xylene with ammonia in the presence of oxygen or a mixture thereof with inert gases and a catalyst; as the latter use is made of a mixture of oxides of bismuth, antimony, molybdenum and chromium taken in a molar ratio of 1–15:1–10:0.5–5:0.5–20 respectively or a mixture of oxides of bismuth, antimony, molybdenum and vanadium taken in a molar ratio of 1–20:1–10:0.1–15:1–20 respectively deposited onto a support.

4 Claims, No Drawings

PROCESS FOR PRODUCING PHTHALONITRILE

The present invention relates to processes for producing aromatic nitriles and, more specifically, it relates to a process for producing phthalonitrile employed as an intermediate product in the production of pigments, dyes, varnishes, stabilizing agents and other materials.

Known in the art is a process for producing phthalonitrile by way of interaction of o-xylene with ammonia in the presence of oxygen or a mixture thereof with inert gases and a catalyst consisting of vanadium oxide and chromium oxide deposited onto alumina.

The yield of phthalonitrile is 70 mol.%.

The yield of phthalonitrile per liter of the catalyst per hour is about 100 g.

This prior art process has a disadvantage residing in a low yield of phthalonitrile from 1 liter of the catalyst per hour due to a low selectivity and capacity of the catalyst.

Known in the art is a process for the production of phthalonitrile by reacting o-xylene with ammonia and oxygen in the presence of a catalyst consisting of a mixture of oxides of cobalt, chromium, manganese, tungsten and potassium deposited onto alumina. The yield of phthalonitrile is 64 mole.%.

This prior art process has a disadvantage residing in a low yield of phthalonitrile due to a low selectivity of the catalyst employed.

Known in the art is a process for producing phthalonitrile by way of reacting o-xylene with ammonia in the presence of oxygen or a mixture thereof with inert gases taken in the molar ratio of 2.9:14.3:82.6 respectively and a catalyst consisting of 5.2% by weight of vanadium pentoxide, 5.8% by weight of antimony trioxide, 0.8% by weight of iron oxide, 0.25% by weight of potassium and 87.95% by weight of alumina.

The process is performed at the temperature of 460° C, contact time of 1.2 sec. The yield of phthalonitrile is 78.8 mol.%. The phthalonitrile output per liter of the catalyst per hour is 100 to 120 g.

In this prior art process phthalonitrile is also produced in the presence of a catalyst consisting of a mixture of oxides of vanadium, antimony and potassium which are deposited onto alumina.

The yield of phthalonitrile in the presence of these catalysts is 82.2 and 78.6 mol.% respectively. The output of phthalonitrile per liter of the catalyst per hour is in both cases about 120 g.

This prior art process has a disadvantage residing in a low yield of phthalonitrile as calculated per liter of a catalyst per hour due to a low selectivity and capacity of the catalyst employed. An essential disadvantage of the above-described prior art processes resides in the formation of substantial amounts of by-products such as o-tolunitrile, benzonitrile, phthalimide which considerably hinder separation and purification of the desired product.

It is an object of the present invention to increase the yield of phthalonitrile.

This object is accomplished by that in a process for producing phthalonitrile by reacting o-xylene with ammonia in the presence of oxygen or a mixture thereof with inert gases and a catalyst at a temperature within the range of from 350° to 500° C, followed by isolation of the desired product, in accordance with the present invention as the catalyst use is made of a mixture of oxides of bismuth, antimony, molybdenum and chromium taken in a molar ratio of 1-15:1-10:0.5-5:0.5-20 respectively or a mixture of oxides of bismuth, antimony, molybdenum and vanadium taken in a molar ratio of 1-20:1-10:0.1-15:1-20 respectively deposited onto a support.

It is preferable, in order to increase the yield of phthalonitrile, to use, as the catalyst, a mixture of oxides of bismuth, antimony, molybdenum and chromium in the molar ratio of 1:2:2.5:0.5 respectively or a mixture of bismuth, antimony, molybdenum and vanadium taken in the molar ratio of 1:2.5:1:2 respectively deposited onto a support.

It is advisable, in order to increase the catalyst productivity and selectivity, to use as the catalyst alumina calcined at a temperature within the range of from 800° to 1,000° C, silica gel or alumosilicate.

The process for producing phthalonitrile according to the present invention is preferably embodied in the following manner.

Through a reactor with a stationary or fluidized bed of a catalyst, a mixture of o-xylene, ammonia, oxygen taken in a molar ratio of 1:4–35:5–40 respectively or said mixture with inert gases at a temparature within the range of from 350° to 500° C and at a space rate of 0.15 to 0.30 hr$^{-1}$.

A vapour-gas mixture after the reactor is condensed with a subsequent recovery of phthalonitrile.

In the process, two types of the catalyst are used: a catalyst consisting of a mixture of oxides of bismuth, antimony, molybdenum and chromium taken in a molar ratio of 1-15:1-10:0.5-5:0.5-20, preferably 1:2:2.5:0.5 respectively deposited onto alumina, silica gel or alumosilicate at a weight ratio of the oxide mixture to the support equal to 1-45:99-55; or a catalyst consisting of a mixture of oxides of bismuth, antimony, molybdenum and vanadium taken in a molar ratio of 1-20:1-10:0.1-15:1-20 respectively, preferably 1:2.5:1:2 deposited onto alumina calcined at the temperature of 900° C, silica gel or alumosilicate at a weight ratio between the oxide mixture and the support equal to 1-45:99-55 respectively.

The catalyst is prepared in the following manner. To an acidic solution of bismuth nitrate, at a temperature of from 30° to 40° C under constant stirring, there are added corresponding amounts of soluble salts of antimony, molybdenum and chromium or vanadium, whereafter the solution temperature is brought to 80°–90° C and the support is added thereto. At this temperature the solution is allowed to stay for 5 to 6 hours, whereafter it is evaporated.

The resulting mass comprising the support impregnated with the above-mentioned salts is dried for a period of 10 to 12 hours at a temperature within the range of from 150° to 200° C, then calcined in a current of air at a temperature ranging from 500 to 600 hours for a period of from 6 to 8 hours.

As a result, a catalyst is obtained consisting of a mixture of oxides of antimony, bismuth, molybdenum and chromium or a mixture of bismuth, antimony, molybdenum and vanadium deposited onto the support.

An advantage of the process for producing phthalonitrile according to the present invention over the prior art processes resides in that the output of phthalonitrile from liter of the catalyst per hour is as high as 270 g due to increased selectivity and capacity of the catalyst.

The amount of by-products is substantially reduced due to the increased catalyst selectivity. These by-products constant of 6–7% by weight of carbon dioxide, 2–3% by weight of o-toluonitrile and 0.5–1% by weight of phthalimide.

For a better understanding of the present invention some examples illustrating the process for producing phthalonitrile are given hereinbelow.

EXAMPLE 1

Through a reactor with a fluidized bed of a catalyst a mixture of o-xylene, ammonia and oxygen taken in the molar ratio of 1:8:8 respectively is passed at the temperature of 420° C and space rate of o-xylene supply of 0.3 hr$^{-1}$. The resulting vapour-gas mixture after the reactor is condensed with a subsequent isolation of the desired product. The catalyst consists of a mixture of oxides of bismuth, antimony, molybdenum and chromium taken in the molar ratio of 1:2:2.5:0.5 respectively deposited onto alumina calcined at the temperature of 900° C at the weight ratio of the oxide mixture to the support of 3:7. Conversion of o-xylene is 95%. The yield of phthalonitrile as calculated for the o-xylene passed through the reactor is 87.4 mol.%.

Output of phthalonitrile is 270 g/l of the catalyst per hour.

EXAMPLE 2

Through a reactor with a fluidized bed of a catalyst a mixture of o-xylene, ammonia and oxygen taken in the molar ratio of 1:10:15 respectively is passed at the temperature of 440° C and space rate of o-xylene supply of 0.3 hr$^{-1}$. The catalyst consists of a mixture of oxides of bismuth, antimony, molybdenum and chromium taken in the molar ratio of 1:1:2:3 respectively deposited onto alumina calcined at the temperature of 1,000° C, at the weight ratio between the oxide mixture and the support equal to 1:4.

Conversion of o-xylene is 100%.

Output of phthalonitrile is 241 g/l of the catalyst per hour.

The yield of phthalonitrile as calculated for the o-xylene passed through the reactor is 78 mol.%.

EXAMPLE 3

Through a reactor with a stationary bed of a catalyst a mixture of o-xylene, ammonia and oxygen taken in the molar ratio of 1:15:10 respectively is passed at the temperature of 380° C and space rate of o-xylene supply of 0.2 hr$^{-1}$. As the catalyst use is made of a catalyst having composition similar to that described in the foregoing Example 1. Conversion of o-xylene is 86%. The yield of phthalonitrile as calculated for the o-xylene passed through the reactor is 72 mol.%. Output of phthalonitrile is 155 g/l of the catalyst per hour.

EXAMPLE 4

Through a reactor with a fluidized bed of a catalyst a mixture of o-xylene, ammonia and oxygen taken in the molar ratio of 1:10:20 respectively is passed at the temperature of 420° C and space rate of o-xylene supply of 0.3 hr$^{-1}$.

The catalyst consists of a mixture of oxides of bismuth, antimony, molybdenum and chromium taken in the molar ratio of 2:1:1:4 respectively deposited on silica gel at the weight ratio between the mixture of the oxides and the support equal to 1:6. Conversion of o-xylene is 90%. The yield of phthalonitrile as calculated for the o-xylene passed through the reactor is 63 mol.%. Output of phthalonitrile is 195 g/l of the catalyst per hour.

EXAMPLE 5

Through a reactor with a fluidized bed of a catalyst a mixture of o-xylene, ammonia and air taken in the molar ratio of 1:10:25 respectively is passed at the temperature of 340° C and space rate of o-xylene supply of 0.25 hr$^{-1}$. The catalyst consists of a mixture of oxides of bismuth, antimony, molybdenum and chromium taken in the molar ratio of 5:10:3:17 respectively deposited onto alumina calcined at the temperature of 800° C at the weight ratio between the oxide mixture and the support equal to 15:85. Conversion of o-xylene is 40%. The yield of phthalonitrile as calculated for the o-xylene passed through the reactor is 20 mol.%. Output of phthalonitrile is 51 g/l of the catalyst per hour.

EXAMPLE 6

Through a reactor with a stationary bed of a catalyst a mixture of o-xylene, ammonia and oxygen taken in the molar ratio of 1:12:8 respectively is passed at the temperature of 380° C and space rate of o-xylene supply of 0.3 hr$^{-1}$.

The catalyst consists of a mixture of oxides of bismuth, antimony, molybdenum and chromium taken in the molar ratio of 10:3:3.5:7.5 respectively deposited onto alumosilicate at the weight ratio between the oxide mixture and the support equal to 35:65.

Conversion of o-xylene is 60%. The yield of phthalonitrile as calculated for the o-xylene passed through the reactor is 36 mol.%. Output of phthalonitrile is 108 g/l of the catalyst per hour.

EXAMPLE 7

Through a reactor with a fluidized bed of a catalyst a mixture of o-xylene, ammonia and oxygen taken in the molar ratio of 1:15:6 respectively is passed at the temperature of 480° C and space rate of o-xylene supply of 0.3 hr$^{-1}$.

The catalyst consists of a mixture of oxides of bismuth, antimony, molybdenum and chromium taken in the molar ratio of 15:4:3.5:2 respectively deposited onto alumosilicate at the weight ratio between the oxide mixture and the support equal to 27:73. Conversion of o-xylene is 100%. The yield of phthalonitrile as calculated for the o-xylene passed through the reactor is 35 mol.%. Output of phthalonitrile is 105 g/l of the catalyst per hour.

EXAMPLE 8

Through a reactor with a fluidized bed of a catalyst a mixture of o-xylene, ammonia and air taken in the molar ratio of 1:20:10 respectively is passed at the temperature of 400° C and space rate of o-xylene supply of 0.3 hr$^{-1}$.

The catalyst consists of a mixture of oxides of bismuth, antimony, molybdenum and chromium taken in the molar ratio of 1:2:5:6 respectively deposited onto silica gel at the weight ratio between the oxide mixture and the support equal to 30:70. Conversion of o-xylene is 85%. The yield of phthalonitrile as calculated for the o-xylene passed through the reactor is 60 mol.%. Output of phthalonitrile is 180 g/l of the catalyst per hour.

EXAMPLE 9

Through a reactor with a fluidized bed of a catalyst a mixture of o-xylene, ammonia and air taken in the molar ratio of 1:10:35 respectively is passed at the temperture of 420° C and space rate of o-xylene supply of 0.3 hr$^{-1}$.

The catalyst consists of a mixture of oxides of bismuth, antimony, molybdenum and chromium taken in the molar ratio of 4:7:0.5:10 respectively deposited on alumina calcined at the temperature of 900° C, at the weight ratio between the mixture of the oxides and the support equal to 35:65.

Conversion of o-xylene is 100%. The yield of phthalonitrile as calculated for the o-xylene passed through the reactor is 70 mol.%. Output of phthalonitrile is 210 g/l of the catalyst per hour.

EXAMPLE 10

Through a reactor with a stationary bed of a catalyst a mixture of o-xylene, ammonia and air taken in the molar ratio of 1:12:40 respectively is passed at the temperature of 360° C and space rate of o-xylene supply of 0.3 hr$^{-1}$.

The catalyst consists of a mixture of oxides of bismuth, antimony, molybdenum and vanadium taken in the molar ratio of 1:2.5:1:2 respectively deposited onto silica gel at the weight ratio between the oxide mixture and the support equal to 1:7. Conversion of o-xylene is 65%. The yield of phthalonitrile for the o-xylene passed through the reactor is 51 mol.%. Output of phthalonitrile is 153 g/l of the catalyst per hour.

EXAMPLE 11

Through a reactor with a fluidized bed of a catalyst a mixture of o-xylene, ammonia and oxygen taken in the molar ratio of 1:8:25 respectively is passed at the temperature of 420° C and space rate of o-xylene supply of 0.3 hr$^{-1}$. The catalyst is similar to that described in the foregoing Example 10. Conversion of o-xylene is 96%. The yield of phthalonitrile as calculated for the o-xylene passed through the reactor is 87.4 mol.%. Output of phthalonitrile is 270 g/l of the catalyst per hour.

EXAMPLE 12

Through a reactor with a stationary bed of a catalyst a mixture of o-xylene, ammonia and oxygen taken in the molar ratio of 1:10:8 respectively is passed at the temperature of 400° C and space rate of o-xylene supply of 0.3 hr$^{-1}$.

The catalyst consists of a mixture of oxides of bismuth, antimony, molybdenum and vanadium taken in the molar ratio of 2:4:1.5:3 respectively deposited onto alumosilicate at the weight ratio between the oxide mixture and support equal to 1:12.

Conversion of o-xylene is 85%. The yield of phthalonitrile as calculated for the o-xylene passed through the reactor is 70 mol.%. Output of phthalonitrile is 217 g/l of the catalyst per hour.

EXAMPLE 13

Through a reactor with a fluidized bed of a catalyst a mixture of o-xylene, ammonia and oxygen taken in the molar ratio 1:15:8 respectively is passed at the temperature of 400° C and space rate of o-xylene supply of 0.2 hr$^{-1}$.

The catalyst consists of a mixture of oxides of bismuth, antimony, molybdenum and vanadium taken in the molar ratio of 5:3:1.5:7 respectively deposited onto alumina calcined at the temperature of 900° C, at the weight ratio between the oxide mixture and the support equal to 1:9.

Conversion of o-xylene is 95%. The yield of phthalonitrile as calculated for the o-xylene passed through the reactor is 72 mol.%. Output of phthalonitrile is 106 g/l of the catalyst per hour.

EXAMPLE 14

Through a reactor with a stationary bed of a catalyst a mixture of o-xylene, ammonia and air taken in the molar ratio of 1:14:45 respectively is passed at the temperature of 380° C and space rate of o-xylene supply of 0.15 hr$^{-1}$.

The catalyst consists of a mixture of oxides of bismuth, antimony, molybdenum and vanadium taken in the molar ratio of 10:2:7:4 respectively deposited onto silica gel at the weight ratio between the oxide mixture and the support equal to 1:4. Conversion of o-xylene is 84%. The yield of phthalonitrile as calculated for the o-xylene passed through the reactor is 40 mol.%. Output of phthalonitrile is 62 g/l of the catalyst per hour.

EXAMPLE 15

Through a reactor with a fluidized bed of a catalyst a mixture of o-xylene, ammonia and oxygen taken in the molar ratio of 1:10:10 respectively is passed at the temperature of 420° C and space rate of o-xylene supply of 0.3 hr$^{-1}$.

The catalyst consists of a mixture of oxides of bismuth, antimony, molybdenum and vanadium taken in the molar ratio of 13:6:0.2:10 respectively deposited onto alumina calcined at the temperature of 900° C, at the weight ratio between the oxide mixture and the support equal to 18:82.

Conversion of o-xylene is 88%. The yield of phthalonitrile as calculated for the o-xylene passed through the reactor is 42 mol.%. Output of phthalonitrile is 130 g/l of the catalyst per hour.

EXAMPLE 16

Through a reactor with a fluidized bed of a catalyst a mixture of o-xylene, ammonia and oxygen taken in the molar ratio of 1:14:10 respectively is passed at the temperature of 440° C and space rate of o-xylene supply of 0.15 hr$^{-1}$.

The catalyst consists of a mixture of oxides of bismuth, antimony, molybdenum and vanadium taken in the molar ratio of 16:7:10:16 respectively deposited onto silica gel at the weight ratio between the oxide mixture and the support equal to 1:3.

Conversion of o-xylene is 96%. The yield of phthalonitrile as calculated for the o-xylene passed through the reactor is 48 mol.%. Output of phthalonitrile is 74.8 g/l of the catalyst per hour.

EXAMPLE 17

Through a reactor with a fluidized bed of a catalyst a mixture of o-xylene, ammonia and oxygen taken in the molar ratio of 1:16:12 respectively is passed at the temperature of 360° C and space rate of o-xylene supply of 0.3 hr$^{-1}$.

The catalyst consists of a mixture of oxides of bismuth, antimony, molybdenum and vanadium taken in the molar ratio of 20:1:15:8 respectively and deposited onto alumosilicate at the weight ratio between the oxide mixture and the support equal to 10:90.

Conversion of o-xylene is 46%. The yield of phthalonitrile as calculated for the o-xylene passed through the reactor is 25 mol.%. Output of phthalonitrile is 77 g/l of the catalyst per hour.

EXAMPLE 18

Through a reactor with a stationary bed of a catalyst a mixture of o-xylene, ammonia and air taken in the molar ratio of 1:14:30 respectively is passed at the temperature of 400° C and space rate of o-xylene supply of 0.25 hr$^{-1}$.

The catalyst consists of a mixture of oxides of bismuth, antimony, molybdenum and vanadium taken in the molar ratio of 1:5:2:20 deposited onto alumina calcined at the temperature of 1,000° C, at the weight ratio between the oxide mixture and the support equal to 1:40.

Conversion of o-xylene is 78%. The yield of phthalonitrile as calculated for the o-xylene passed through the reactor is 43 mol.%. Output of phthalonitrile is 107 g/l of the catalyst per hour.

What is claimed is:

1. A process for producing phthalonitrile comprising reacting o-xylene with ammonia at a temperature ranging from 350° to 550° C in the presence of oxygen or a mixture thereof with inert gases and a catalyst selected from the group consisting of a mixture of oxides of bismuth, antimony, molybdenum and chromium taken in a molar ratio of 1-15:1-10:0.5-5:0.5-20 respectively, and a mixture of oxides of bismuth, antimony, molybdenum and vanadium taken in a molar ratio of 1-20:1-10:0.1-15:1-20 respectively, deposited onto a support, followed by isolation of the desired product.

2. A process as claimed in claim 1, wherein as the catalyst use is made of a mixture of oxides of bismuth, antimony, molybdenum and chromium taken in the molar ratio of 1:2:2.5:0.5 respectively deposited onto a support.

3. A process as claimed in claim 1, wherein as the catalyst use is made of a mixture of oxides of bismuth, antimony, molybdenum and vanadium taken in the molar ratio of 1:2.5:1:2 respectively deposited onto a support.

4. A process as claimed in claim 1, wherein use is made of a support selected from the group consisting of alumina calcined at a temperature ranging from 800° to 1,000° C, silica gel and alumosilicate.

* * * * *